United States Patent [19]
Woo et al.

[11] Patent Number: 4,584,875
[45] Date of Patent: Apr. 29, 1986

[54] CONTINUOUS MEASUREMENT OF YARN TWIST

[75] Inventors: Jae L. Woo, Eastwood; Boshra D. Farah, Kogarah, both of Australia

[73] Assignee: Unisearch Limited, Kensington, Australia

[21] Appl. No.: 606,774

[22] PCT Filed: Aug. 12, 1983

[86] PCT No.: PCT/AU83/00109
§ 371 Date: Apr. 12, 1984
§ 102(e) Date: Apr. 12, 1984

[87] PCT Pub. No.: WO84/00781
PCT Pub. Date: Mar. 1, 1984

[30] Foreign Application Priority Data
Aug. 12, 1982 [AU] Australia .............................. PF5359

[51] Int. Cl.⁴ .............................................. G01H 17/00
[52] U.S. Cl. ........................................ 73/160; 57/264; 73/651
[58] Field of Search ................ 73/570, 658, 651, 160; 57/264, 265; 310/321, 323, 338, 25

[56] References Cited
U.S. PATENT DOCUMENTS

| | | | |
|---|---|---|---|
| 3,273,380 | 9/1966 | Seney | 73/160 |
| 3,613,347 | 10/1971 | Carruthers | 73/160 |
| 4,133,207 | 1/1979 | Weidmann et al. | 73/160 |
| 4,295,360 | 10/1981 | Fountain | 73/160 |
| 4,330,094 | 5/1982 | Mayer | 57/265 |

FOREIGN PATENT DOCUMENTS
1405555 9/1975 United Kingdom .

*Primary Examiner*—Stephen A. Kreitman
*Attorney, Agent, or Firm*—Bacon & Thomas

[57] ABSTRACT

A method and apparatus for non-destructively measuring twist in a translating yarn (2) by means of a blade (1) which is in rubbing contact with the translating yarn (2) so that vibrations are imparted to the blade (1). The frequency of vibration of the blade (1) provides a measure of the twist imparted to the yarn (2) so that the signal frequency can be used as a measurement of the twist in a yarn (2) under test or as a feedback signal controlling the rate of twist imparted by a twist insertion station (8) during the formation of a yarn.

10 Claims, 3 Drawing Figures

CONTINUOUS MEASUREMENT OF YARN TWIST

TECHNICAL FIELD

The present invention relates to a method and means for measuring the amount of twist in a travelling length of yarn and in particular to a non-destructive method for carrying out twist measurement.

BACKGROUND ART

Existing methods and means for measuring twist in yarn, for the most part, rely on the measurement of the twist angle alone and take no account of the important fact that the twist being measured is dependent upon the ever-varying yarn diameter. Such methods include a ply-twist method of measurement wherein a sample of yarn is untwisted in order to determine the twist that has been imparted to the yarn. Another method provides an untwist-twist technique wherein the yarn extends while being untwisted and contracts while being twisted in the opposite sense of its original twist so that when the original length of the yarn is attained during twisting in the opposite sense the total number of revolutions from untwist to twist is deemed to be twice the total twist of the length of yarn under test. Another method as shown in G.B. No. 1,266,450 proposes measurement of twist as the yarn is being formed at a point upstream of the twist spindle while the yarn is rotating.

The existing devices and methods use one of the following techniques:

(1) obtain a measurement of twist from two measured quantities—twist-angle and the yarn "diameter";

(2) obtain a measure of twist as the ratio of the specimen's tendency-to-rotate to the yarn speed necessitating the specimen to be actually in the process of twist insertion;

(3) use the twist-angle as a measure of the yarn twist ignoring the variation in the yarn "diameter".

DISCLOSURE OF INVENTION

The present invention proposes a method and means of measurement of twist in a rotating or non-rotating continuous travelling yarn which may be effected subsequent to the formation of the twisted yarn.

In one aspect the present invention provides a method of measuring twist in a translating yarn comprising sensing the frequency of vibration of a blade having an edge in contact with the translating yarn and calculating the twist of the yarn which is a function of the frequency of vibration of said blade.

In another aspect the present invention provides apparatus for measuring twist in a translating yarn comprising a blade adapted to have an edge in contact with a translating yarn, means for sensing the vibration imparted to said blade by the translation of said yarn across said edge, and means for measuring the frequency of said vibration.

This invention measures the twist in a translating yarn, whether it is rotating or not, continuously and non-destructively, by sensing the frequency of vibration of a blade which is in contact with the moving specimen, and amplifying, processing and displaying or printing the time-varying signal obtained therefrom.

The twist estimated by the new device and method is an accurate and precise measure of twist of a running yarn as will be appreciated by the facts:

(1) what is being sensed by the vibrating blade is the real twist itself;

(2) the measureand is independant of the yarn "diameter" variation; and (3) only a single measurand is needed.

BRIEF DESCRIPTION OF DRAWINGS

The present invention will now be described by way of example with reference to the accompanying drawings, in which.

MODES FOR CARRYING OUT THE INVENTION

Figure 1:
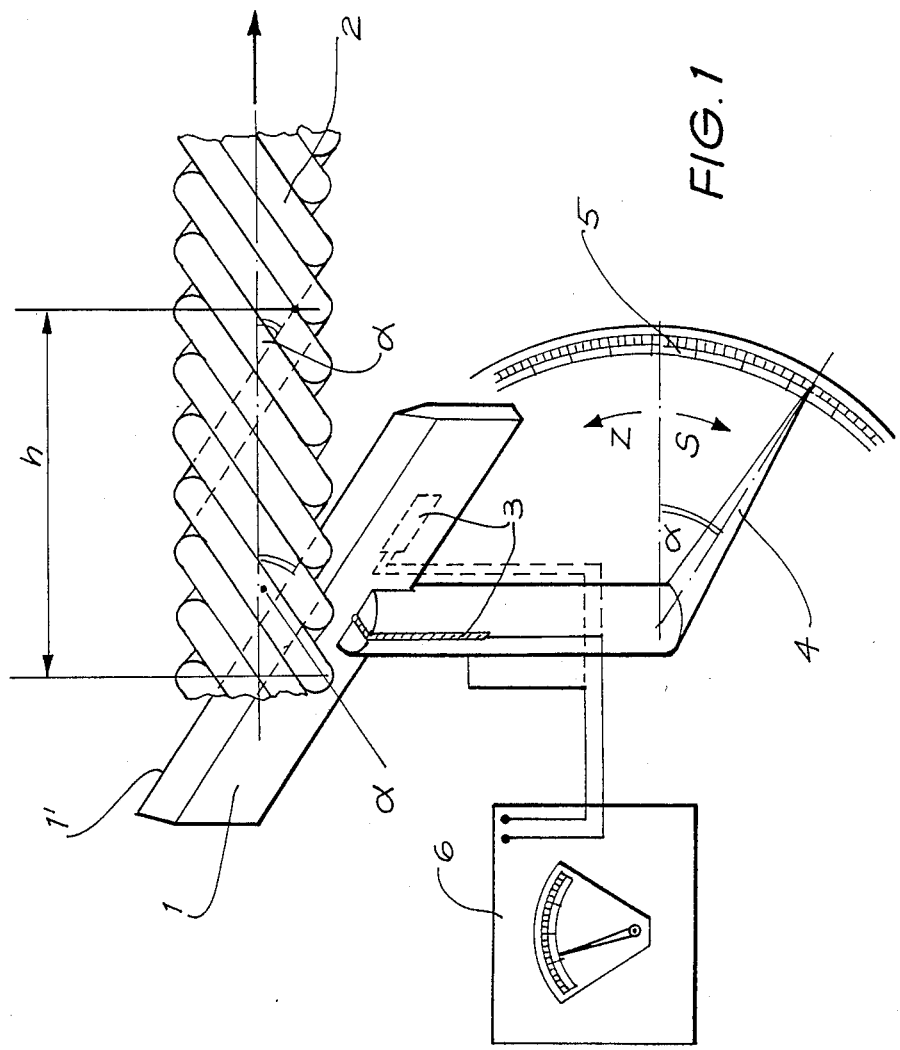
FIG. 1 is a schematic view of apparatus in accordance with a first embodiment of the present invention.

Referring to FIG. 1 which shows a vibration sensing blade 1 with its edge 1' placed so as to remain in contact with moving yarn 2. Blade 1 vibrates as yarn 2 moves across edge 1'; such vibration depends upon blade design and dimensions, yarn tension, speed and surface properties but mainly the surface twist angle $\alpha$. By turning blade 1 around its pivot axis, a maximum amplitude of vibration will be evident where the blade edge 1' is parallel to yarn elements on the surface of yarn 2 (e.g. filaments and fibres in case of a single yarn, or single yarns in case of ply yarns). Thus at the maximum amplitude position the angle between blade edge 1' and the axis of yarn 2 will indicate the yarn's surface twist angle $\alpha$ as represented by twist-angle pointer 4 against scale 5.

For an ideal case where the yarn has constant twist and constant diameter, i.e. the surface twist angle $\alpha$ has a constant value, the blade 1 should have only one position at which blade vibration has its maximum amplitude giving the twist angle $\alpha$. Furthermore, at constant yarn speed and tension the vibration frequency would be constant and correspond to the constant amount of twist. In the ideal case the yarn twist could be readily calculated using $\alpha$ and the yarn diameter according to the following:

$$T = (\tan \alpha)/\pi d \qquad (1)$$

T = yarn twist in turns/cm
d = yarn diameter in cm

Figure 2:
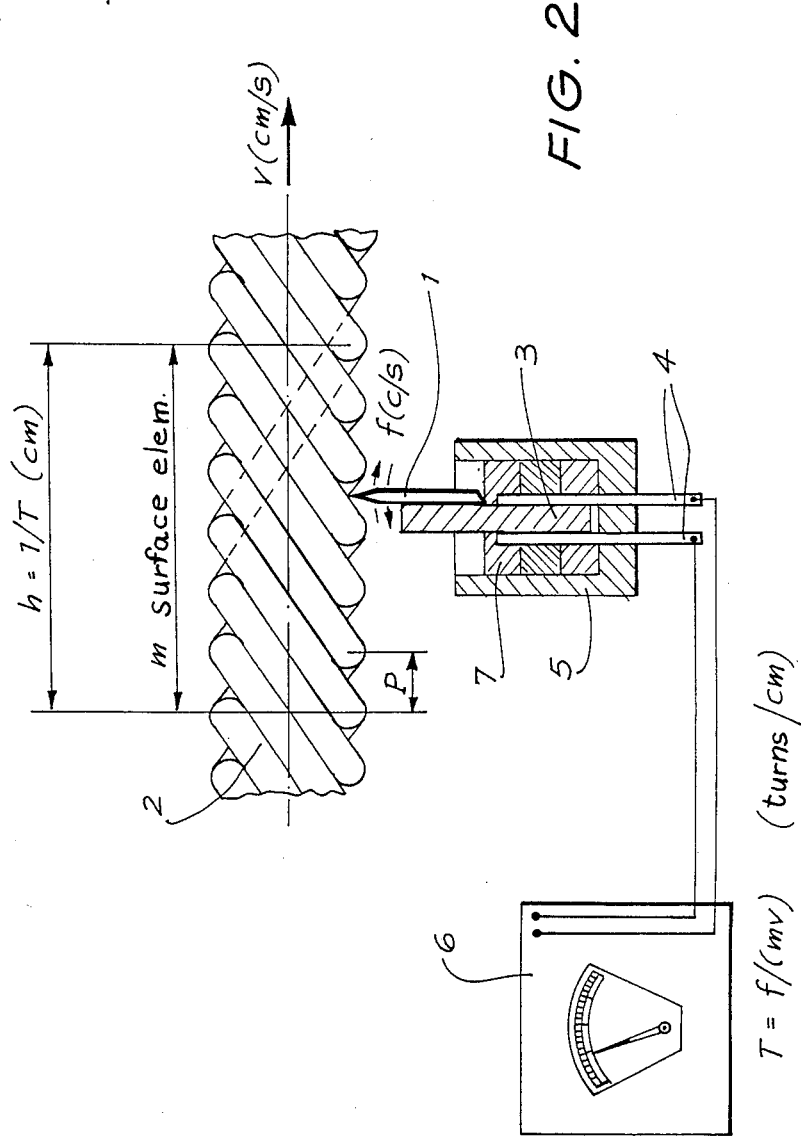
FIG. 2 is a schematic view of apparatus in accordance with a second embodiment of the present invention.

As yarns in practice have variable diameters and twist, i.e. variable surface twist angle $\alpha$, then the procedure adopted with the apparatus of FIG. 1 is to adjust blade 1 and fix it at a specified position. Yarn twist is measured by sensing the frequency of the blade vibration. The selected blade position has its effect on the vibration amplitude. For a relatively long blade, as shown in FIG. 1, it is preferable to fix the blade with its edge as close as possible to the maximum amplitude position; i.e. the angle between the blade 1 and the axis of yarn 2 is as near as possible to the nominal twist angle $\alpha$. For a very short blade, as shown in FIG. 2, it may be mounted with its edge perpendicular to the yarn axis and fixed at that position for all twist varieties.

For a specific yarn 2 at particular adjustments relative to the blade 1 and at a predetermined yarn speed there is a very high correlation between blade vibration frequencies and twist values of the yarn under test. The regression coefficients (T/f) (where T=twist and f=frequency of vibration) can easily be determined by conducting calibration tests related to the yarn under test and the speed to be used. If the tested yarn has regular twist, the blade vibration frequency will be constant. If the twist varies higher or lower than the nominal value then the resulting vibration frequency will be commensurately higher or lower than the frequency corresponding to the nominal twist.

Vibrations imparted to blade 1 are sensed by vibration sensing elements 3 which output signals to converter 6 which transfers the vibration frequencies of blade 1 into twist values. Converter 6 includes appropriate electric circuits and filters providing the frequency of vibration of blade 1 as sensed by elements 3, which may be strain gauges or the like, due to the passage of yarn 2. Appropriate electric circuits and filters provide the frequency of the signal which only corresponds to yarn twist and cut-off the frequencies due to the natural frequency of the blade or due to the noise effects.

An embodiment constructed according to FIG. 1 using a steel blade 38.0×8.0×0.25 mm. employs a pair of strain gauges 3 for sensing the vibrations of the blade, one is mounted on each side of the blade 1. Strain gauges 3 are coupled to a Wheatstone bridge included in a strain gauge indicator; the output of the latter passes through a high-pass filter to cut off the frequencies due to noise and due to the electric current, and through a low-pass filter to cut-off the natural frequency of the blade. The output signal from the filters is received by a universal counter to count the corresponding frequency within a preselected time interval and it displays the average frequency. According to this embodiment the natural frequency of the blade ranges to about 800 Hz. To avoid the interference of the natural frequency of the blade as well as of the noise, the band-pass filters have to be set up such that 200 Hz<working range<600 Hz. Therefore, this arrangement may work successfully for plied or cabled yarns running at slow speeds. For example for cabled yarn/3 singles with nominal twist of 3 turns/cm, this embodiment may be used for continuous twist measurement for speeds between 13 and 40 m/min.

To overcome the speed limit and to apply this method for single yarns as well, the device is modified using a very small (miniature) blade 2.0×5.00×0.25 mm. For this embodiment it is more convenient to use piezo electric bimorph as a vibration sensing element instead of the strain gauges. FIG. 2 shows a schematic drawing of this embodiment wherein the yarn 2 passes across the edge of the miniature blade 1, which is glued on one side of the piezo electric bimorph 3. The bimorph 3 is mounted cantilever fashion between the two poles 4 which are fixed in casing 5 made of insulating material. The bimorph 3 and the poles 4 are surrounded by rubber rings 7 as acoustic insulating packings. The piezo electric bimorph 3 as a generator; it transfers the mechanical vibration of the blade-end into alternating electric current at the poles 4. For every mechanical vibration of the blade 1, an electric wave of one cycle is produced at the pole 4. The output signal is received by the converter 6 which includes appropriate electric circuits and filters to process the signal, display and/or compute the twist values. Using this embodiment, the natural frequency of the blade could be higher than, say 5 kHz. The working range of this version may be: 200 Hz<working range<4 kHz which can accomodate twist measurements at higher speeds as well as the twist measurements of single yarns. For example for the same cabled yarn mentioned before (3 singles with 3 turns/cm) this embodiment is capable of measuring ply twist at speeds between 15 and 270 m/min.

Theoretical aspects of the present invention are explained in reference to FIG. 2, where the yarn 2 is assumed to have a "helical multi-thread" on its surface with the following parameters:

m: number of helical threads on yarn surface=number of yarn surface elements, i.e. number of filaments or fibres on single yarn surface or number of single yarns on cabled or plied yarn surface.

T: yarn twist in turns/cm h: lead of a helical thread, i.e. the length of one turn of twist in cm, or $$h = (1/T) \quad (2)$$

p: pitch in cm, i.e. the distance between two consecutive crests, or $$T = (h/m) \quad (3)$$

If the yarn 2 moves with a velocity of v cm/s crossing the blade 1, assuming every passing crest of the serrated profile of yarn surface will impart one pulse to the blade, then the blade will vibrate with a frequency f Hz, where $$f = (v/p) \quad (4)$$

By substituting equations (2) and (3) in equation (4), then $$p = (f/mv) \quad (5)$$

The value of (f/v) may be considered as the measuring index $I_b$ of the blade vibration device.

Therefore equation (5) could be written in the general form:

$$T = K_b I_b \quad (6)$$

Where $K_b$ is the proportionality constant.
Under ideal conditions and according to equation (5)

$$K_b = (1/m) \quad (7)$$

This means that in the ideal condition $K_b$ takes the reciprocal value of the number of yarn surface elements m. Its application is clear for ply or cabled yarns where m equals the number of singles taking helical path on yarn surface. For yarns where the total number of constituent elements N (i.e. total number of singles in a cabled yarn) is not greater than 5, then m=N, or $$K_b = (1/N) \text{ for } 2 \leq N \leq 5 \quad (8)$$

For cabled yarns with a total number of constituent singles greater than 5 (or N>5) as well as for single yarns where the number of constituent fibres is mostly >5, in these cases m is not necessarily equal to N. This is because some of the yarn constituent elements exist inside the yarn body as a core and may not appear on the yarn surface. To determine m in these cases, the pattern taken by the yarn constituent elements has to be found out. Accordingly m may be calculated.

Figure 3:
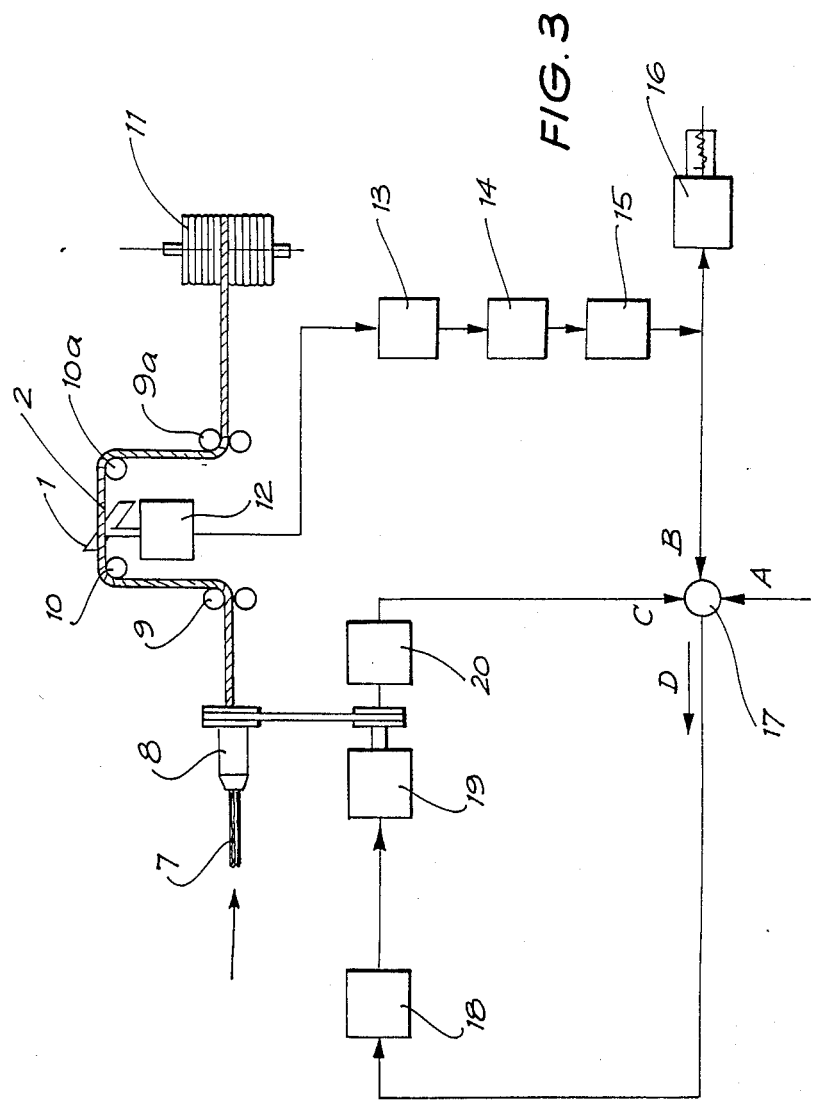
FIG. 3 is a schematic view showing an example of how the apparatus of FIG. 1 or FIG. 2 can be used during the production of twisted yarn.

Referring to FIG. 3 where there is shown apparatus of the type of FIG. 1 or FIG. 2 mounted as an on-line twist sensing and monitoring component of a control system in an open-end spinning process. The input fibre material 7, e.g. sliver, roving or tops, is fed to the twist insertion device 8, e.g., an open-end spinning rotor, and delivered as a spun yarn with constant speed by the nip rollers 9. The yarn 2 runs with constant speed over adjustable guide rollers 10 and 10a passing, in-between, over the twist measuring device 12, in contact with the edge of sensing blade edge 1. The yarn 2 passes through the nip rollers 9a to the winding head 11 such that the yarn tension remains constant. The electric signals coming out of the converter 13 (similar to the converter 6 in FIGS. 1 or 2), which correspond the to the values of blade vibration frequencies and consequently to the twist values, are integrated over a predetermined time period through integrator 14 and a signal corresponding to the mean value is delivered to amplifier 15. The output signal can be received by a pen recorder 16 giving a chart representing the continuous measurement of twist values and/or transmitted to comperator 17. The rate of twist insertion is measured by coupling a tachogenerator 20 to the motor 19, giving an electric signal corresponding to the actual rotational speed of the spinning rotor 8. The comperator 17 is fed with three signals, namely an adjusted nominal value A, a measured value B and the actual twist insertion rate value C, and it delivers the resultant value D. The latter signal D is transmitted to the variable speed device 18 which in turn controls the motor speed so that the yarn twist produced is adjusted to the required nominal twist value and maintained constant at this value.

It will be appreciated that the present invention is not limited by the specifics of the preceding description in relation to the drawings and the addressee will be aware of variations and modifications once apprised of the essential elements of the invention.

It will be recognised by persons skilled in the art that numerous variations and modifications may be made to the invention as described above without departing from the spirit or scope of the invention as broadly described.

We claim:

1. A method of measuring twist in a translating yarn comprising sensing the frequency of vibration of a fixed blade having an edge in contact with the translating yarn and calculating the twist of the yarn which is a function of the frequency of vibration of said blade.

2. A method as claimed in claim 1 wherein the edge of the blade in contact with the yarn is perpendicular to the axis of the yarn where the yarn contacts the blade.

3. A method as claimed in claim 1 wherein the edge of the blade in contact with the yarn is inclined to the axis of the yarn where the yarn contacts the blade, said inclination being such that the amplitude of vibration of the blade, as the yarn is translating, is at a maximum.

4. Apparatus for measuring twist in a translating yarn comprising a fixed blade adapted to have an edge in contact with a translating yarn, means for sensing the vibration imparted to said blade by the translation of said yarn across said edge, and means for measuring the frequency of said vibration.

5. Apparatus as claimed in claim 4 wherein the means for sensing vibration of the blade comprise strain gauges located on opposite sides of the blade.

6. Apparatus as claimed in claim 4 wherein the means for sensing vibration of the blade comprises a piezo electric bimorph.

7. Apparatus as claimed in claim 4 where the output of the sensing means is input to a converter which produces an output proportional to the twist of the translating yarn.

8. Apparatus as claimed in claim 7 where the output of the converter is proportional to the instantaneous twist of the yarn.

9. Apparatus as claimed in claim 7 where the output of the converter is proportional to the average twist of the yarn for predetermined time intervals or lengths of yarn as the yarn is travelling in contact with the edge of the blade.

10. An automatic control system for a twist insertion apparatus comprising: a fixed blade adapted to have an edge in contact with a translating yarn; means for sensing the vibration imparted to said blade by the translation of said yarn across said edge; means for measuring the frequency of said vibration; and, means for providing a feedback signal controlling the twist insertion rate applied to input fibre material at a twist insertion station.

* * * * *

UNITED STATES PATENT AND TRADEMARK OFFICE
CERTIFICATE OF CORRECTION

PATENT NO. : 4,584,875
DATED : April 29, 1986
INVENTOR(S) : Jae L. Woo and Boshra D. Farah It is certified that error appears in the above-identified patent and that said Letters Patent is hereby corrected as shown below:

Col. 4, line 23: "$T = (h/m)$" should read --$p = (h/m)$--

Col. 4, line 36: "$p = (f/mv)$" should read --$T = (f/mv)$--.

Signed and Sealed this

Twelfth Day of August 1986

[SEAL]

Attest:

DONALD J. QUIGG

Attesting Officer

Commissioner of Patents and Trademarks